US00PP14214P29

(12) United States Plant Patent
Bijl

(10) Patent No.: US PP14,214 P2
(45) Date of Patent: Oct. 7, 2003

(54) FERN PLANT NAMED 'VP001'

(50) Latin Name: *Nephrolepis cordifolia*
Varietal Denomination: VP001

(75) Inventor: Jacob Johannes Bijl, Burgh-Haamstede (NL)

(73) Assignee: Vitro Plus CV, Renesse (NL)

( * ) Notice: Subject to any disclaimer, the term of this patent is extended or adjusted under 35 U.S.C. 154(b) by 0 days.

(21) Appl. No.: 10/180,324

(22) Filed: Jun. 27, 2002

(51) Int. Cl.[7] ..... A01H 9/00
(52) U.S. Cl. ..... Plt./379
(58) Field of Search ..... Plt./379

*Primary Examiner*—Bruce R. Campell
*Assistant Examiner*—Michelle Kizilkaya
(74) *Attorney, Agent, or Firm*—Foley & Lardner

(57) ABSTRACT

A new and distinct fern plant named 'VP001' characterized by having densely crowded compact shape; brown downy scales at the base; green leaves; sterile and button shaped leaflets; erect and occasionally forked stalks; good tolerancy against heat; and low humidity.

2 Drawing Sheets

Latin name of genus and species of the plant claimed: *Nephrolepis cordifolia.*
Variety denomination: VP001.

BACKGROUND OF THE INVENTION

The present invention relates to a new and distinct cultivar of fern plant, botanically known as *Nephrolepis cordifolia,* hereinafter referred to by the cultivar name 'VP001'.

The new cultivar originated The Netherlands as a mutant in Renesse, The Netherlands. The parent *Nephrolepis cordifolia* 'Duffii' (also known as 'Lemon Button', unpatented). 'VP001' was discovered and selected by the inventor, Jacob J. Bijl, in a controlled environment in Renesse, The Netherlands.

Asexual reproduction of the new cultivar by leaf cuttings was first performed on Nov. 6, 2000 in Renesse, The Netherlands and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'VP001' which in combination distinguish this fern as a new and distinct cultivar:

1. Densely crowded compact fern;
2. brown downy scales at the base;
3. green leaves;
4. sterile and button shaped leaflets;
5. erect and occasionally forked stalks: and
6. heat and low humidity tolerant.

'VP001' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Renesse, The Netherlands under conditions which closely approximate those generally used in commercial practice.

Of the many commercial cultivars known to the present inventor, the most similar in comparison to 'VP001' is the cultivar 'Duffii'. The growth rate of 'VP001' is much faster than the growth rate of 'Duffii'. The leaflets of 'VP001' are much wider than the leaflets of 'Duffii'.

BRIEF DESCRIPTION OF THE DRAWINGS

The accompanying photographic drawings illustrate the overall appearance of the new fern showing the colors as true as is reasonably possible with colored reproductions of this type.

The first drawing shows a 'VP001' plant on the left and a comparison photo on the right of a 'VP001' leaf and a 'Duffii' leaf.

The second drawing shows an frontal view (upper photo) and a view from above (lower photo) of 'VP001' to the left and 'Duffii' to the right. The plants are 11 weeks of age in both drawings.

DETAILED BOTANICAL DESCRIPTION

The following observations, measurements and values describe the new cultivar as grown in Renesse, The Netherlands under conditions which closely approximate those generally used in commercial practice. 'VP001' is grown in a normal commercial greenhouse in temperatures ranging from 20 to 30 degrees Celsius. Maximum temperature tolerancy is 35 degrees Celsius, minimum temperature tolerancy is 10 degrees Celsius. It takes one week to iniate roots and four weeks to develop roots. Fertilizers: no particulars. In the 15 weeks after pricking the plant grows approximately 30 to 40 cm. Humidity is between 50 and 90 percent. No artificial lighting or photo periodic treatments are added. Color references are made to The Royal Horticultural Society Colour Chart (R.H.S.) 2001 edition, except where general colors of ordinary significance are used. Color values were taken under daylight conditions at approximately 1:30 p.m. in Boskoop, The Netherlands. The age of the plant described is 11 weeks.

Propagation: Tissue culture.

Plant:

*Plant shape.*—Broad upright (inverted triangle) with rather stiff fronds.

*Height.*—Average 20 cm.

*Width.*—Average 25 cm.

*Growth habit.*—Fronds grow from the base of the plants and are rather stiff.

*Growth rate.*—Moderate.

*Vigor.*—Not vigorous.

*Growth and branching habit.*—Fronds grow from the base where short rootstocks are formed. The fronds are rather stiff and grow in an average angle of 70° from the nodes.

*Crop time.*—Year round (greenhouse grown).

*Winter hardiness/weather tolerance.*—USDA zone 10.

Rooting time:

*Rooting habit.*—Freely branching.

*Time to initiate roots.*—1 week.

*Time to develop roots.*—4 weeks.

Frond description:

*Leaf arrangement.*—Fronds crowded (alternate) on the rhizome (rootstock).

*Length.*—Average 16 cm.

*Width.*—Average 3.1 cm.

*Rachis diameter.*—Average 1.1 mm.

*Rachis color.*—Upper side: Green, between RHS 137A and RHS 141A, underside green; RHS 143A. Rachis densely covered with small greenish to silvery-white hairs; these hairs have an average length of approximately 2 mm. On older fronds these hairs are only placed at the pinnae axils and becoming greyed-orange RHS 164B.

Pinnae description:

*Quantity of pinnae per frond.*—Average: 40 (varies from 34 to 56).

*Shape.*—Narrow ovate to narrow triangular; some pinnae vary in shape and size, these are orbicular to ovate and ver small, approximately 5 mm long and 6 mm wide and grow randomly along the rachis, but usually halfway from the base to top of the fronds.

*Length.*—Average 1.6 cm.

*Width.*—Average 1 cm.

*Apex.*—Obtuse.

*Base.*—Truncate to oblique.

*Aspect.*—Pinnae are thin and smooth on both sides.

*Attachment.*—Pinnae attached by vein only.

*Margin.*—Finely crenate.

*Texture.*—Smooth.

*Color of upper surface.*—Mature leaf: Green, RHS 137 A/B. Immature leaf: Green, RHS 143 A.

*Color of lower surface.*—Mature leaf: Green, RHS-CC 137 B. Immature leaf: Green, RHS-CC 143 B.

Flowers: None observed.

*Seeds.*—None observed.

Disease resistance: No particular observations made.

I claim:

1. A new and distinct fern plant named 'VP001', substantially as illustrated and described herein.

* * * * *

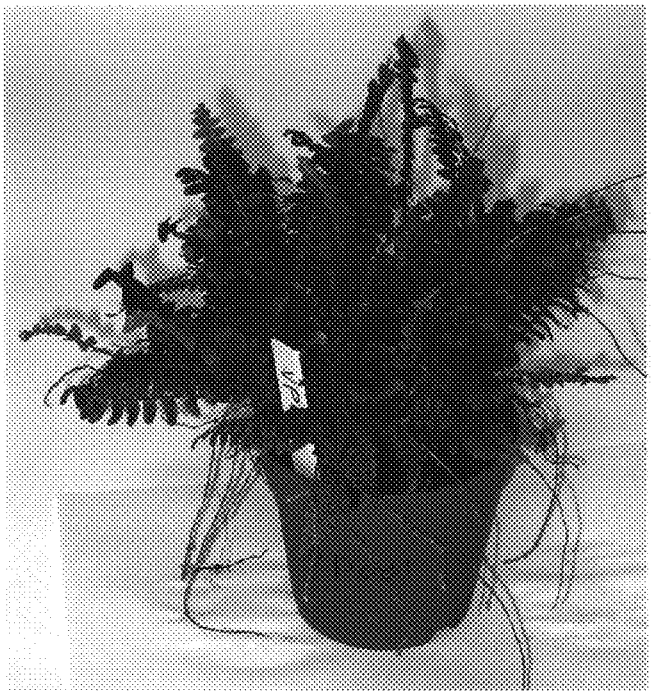
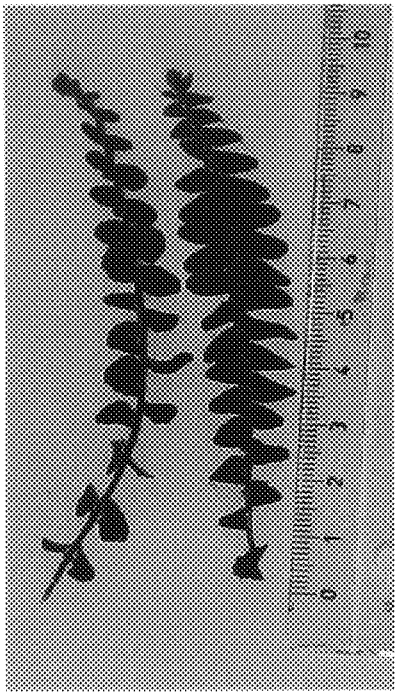

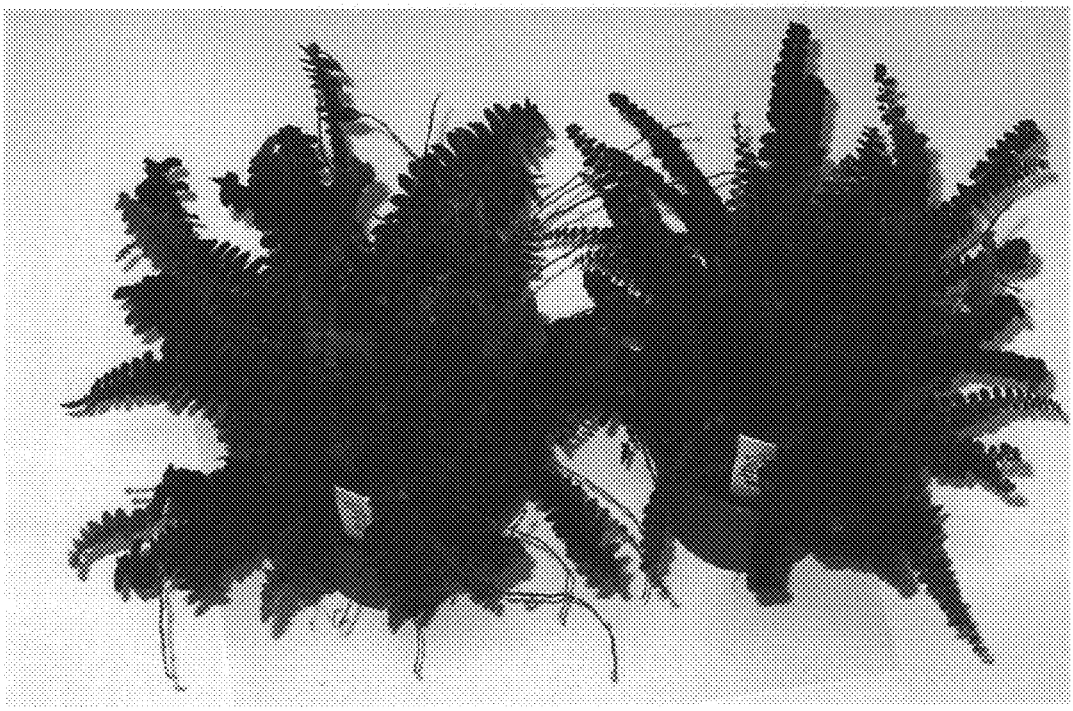

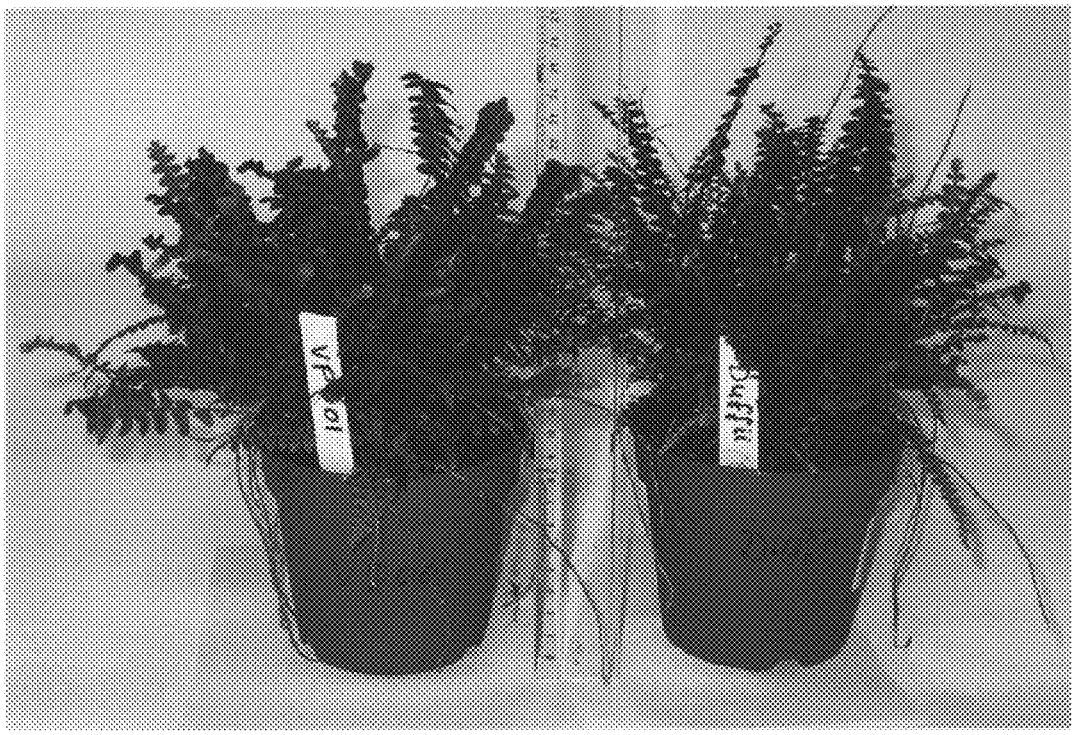
Cuff'n
VT 101